US009610027B2

(12) United States Patent
Hauck et al.

(10) Patent No.: US 9,610,027 B2
(45) Date of Patent: Apr. 4, 2017

(54) CORRECTION OF SHIFT AND DRIFT IN IMPEDANCE-BASED MEDICAL DEVICE NAVIGATION USING MEASURED IMPEDANCES AT EXTERNAL PATCH ELECTRODES

(71) Applicant: St. Jude Medical, Atrial Fibrillation Division Inc, Saint Paul, MN (US)

(72) Inventors: John A. Hauck, Shoreview, MN (US); Jeffery A. Schweitzer, Saint Paul, MN (US); Lev A. Koyrakh, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 164 days.

(21) Appl. No.: 14/471,730

(22) Filed: Aug. 28, 2014

(65) Prior Publication Data
US 2015/0005624 A1 Jan. 1, 2015

Related U.S. Application Data

(63) Continuation of application No. 13/690,737, filed on Nov. 30, 2012, now Pat. No. 8,849,393.

(51) Int. Cl.
*A61B 5/00* (2006.01)
*A61B 5/06* (2006.01)
*A61B 5/053* (2006.01)

(52) U.S. Cl.
CPC ............ *A61B 5/063* (2013.01); *A61B 5/6801* (2013.01); *A61B 5/742* (2013.01); *A61B 5/053* (2013.01)

(58) Field of Classification Search
CPC ..... A61B 5/053; A61B 5/0531; A61B 5/0538; A61B 5/063; A61B 5/6801; A61B 5/742
See application file for complete search history.

(56) References Cited

U.S. PATENT DOCUMENTS 7,263,397 B2 8/2007 Hauck et al.
7,885,707 B2 2/2011 Hauck
(Continued)

FOREIGN PATENT DOCUMENTS

| CN | 101756701 | 6/2010 |
|---|---|---|
| CN | 102525472 | 7/2012 |
| WO | 2007/035339 | 3/2007 |

OTHER PUBLICATIONS

International Search Report and Written Opinion issued in International (PCT) Patent Application No. PCT/US2013/071501 (Feb. 26, 2014).

*Primary Examiner* — Max Hindenburg
(74) *Attorney, Agent, or Firm* — Dykema Gossett PLLC (57) ABSTRACT

A system and method are provided for determining characteristics of a device electrode disposed on a medical device within a body. A plurality of measurement electrodes are coupled to an external surface of the body and establish transmission paths for current through the body. An electronic control unit (ECU) is configured to cause transmission of current between a pair of active electrodes selected from the measurement electrodes and thereby generate a voltage on the device electrode. The ECU receives impedance signals from a plurality of passive electrodes among the measurement electrodes other than the active electrodes. The ECU establishes a virtual reference electrode at a reference position within the body responsive to the impedance signals and computes a position of the device responsive to the voltage on the device electrode and the reference position of the reference electrode. The ECU may also compute impedances at the device and measurement electrodes.

15 Claims, 3 Drawing Sheets

(56) References Cited

U.S. PATENT DOCUMENTS

| | | |
|---|---|---|
| 8,214,007 B2 | 7/2012 | Baker et al. |
| 8,364,253 B2 * | 1/2013 | Voth ..................... A61B 5/042 600/523 |
| 8,517,031 B2 | 8/2013 | MacGregor et al. |
| 8,630,699 B2 | 1/2014 | Baker et al. |
| 8,849,393 B2 * | 9/2014 | Hauck ................. A61B 5/6801 600/547 |
| 2004/0254437 A1 | 12/2004 | Hauck et al. |
| 2007/0060833 A1 | 3/2007 | Hauck |
| 2012/0172715 A1 | 7/2012 | MacGregor et al. |

* cited by examiner

CORRECTION OF SHIFT AND DRIFT IN IMPEDANCE-BASED MEDICAL DEVICE NAVIGATION USING MEASURED IMPEDANCES AT EXTERNAL PATCH ELECTRODES

BACKGROUND a. Field

The present disclosure relates to a system and method for determining one or more characteristics of a device electrode on a medical device within a body, including the position of the device electrode and the measured impedance at the device electrode. In particular, the instant disclosure relates to a system and method that enable correction of drift and shift in position and impedance measurements in electric field based position and navigation systems.

b. Background

A wide variety of medical devices are inserted into the body to diagnose and treat various medical conditions. Catheters, for example, are used to perform a variety of tasks within the body including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is used to puncture the skin surface and a sheath having an inner diameter greater than the outer diameter of the catheter is threaded through the vasculature to a region of interest. The catheter is then moved longitudinally through the sheath to the region of interest either manually by a clinician or through the use of electromechanical drive systems.

Clinicians track the position of medical devices such as catheters as they are moved within the body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and physician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a physician through, for example, a visual display.

One conventional medical device navigation system is made available under the trademark "ENSITE NAVX" by St. Jude Medical, Inc. The system is based on the principle that when electrical currents are passed through the thorax a voltage drop occurs across internal organs such as the heart and this voltage drop can be measured and used to determine the position of a medical device within the body. The system includes three pairs of patch electrodes that are placed on opposed surfaces of the body (e.g., chest and back, left and right sides of the thorax, and neck and leg) and form generally orthogonal x, y, and z axes as well as a reference electrode that is typically placed near the stomach and provides a reference value and acts as the origin of the coordinate system for the navigation system. Sinusoidal currents are driven through each pair of patch electrodes and voltage measurements for one or more electrodes associated with the medical device are obtained. The measured voltages are proportional to the distance of the device electrodes from the patch electrodes. The measured voltages are compared to the potential at the reference electrode and a position of the device electrodes within the coordinate system of the navigation system is determined.

The above-described system can be used to provide a substantially accurate indication of the position of the medical device within a body. Electric field based navigation systems, however, are subject to various types of interference that can impact the accuracy of position measurements. For example, the level of electrical impedance in the patient body is not necessarily constant. The impedance can slowly drift or even undergo transient shifts due to, for example, a change in medication, which can lead to drift and/or shift in the detected position of the medical device. Various methods have been proposed to mitigate potential drift or shift including the use of a fixed reference catheter with a reference electrode and bio-impedance scaling. The use of a fixed reference catheter requires insertion of an additional catheter into the body thereby increasing procedure time and the risk of complications. Further, the reference catheter may become dislodged during the procedure. Bio-impedance scaling is often effective in correcting drift, but does not adequately correct for shifts.

BRIEF SUMMARY

The present disclosure relates to a system and method for determining one or more characteristics of a device electrode on a medical device within a body. In particular, the instant disclosure relates to a system and method that enable correction of drift and shift in position and impedance measurements in electric field based position and navigation systems.

A system in accordance with one embodiment of the present teachings for determining one or more characteristics of a device electrode disposed on a medical device within a body includes an electronic control unit configured to cause transmission of a current between a pair of active electrodes. The pair of active electrodes is selected from among a plurality of measurements electrodes each coupled to an external surface of the body. The transmission of current between the active electrodes generates a voltage on the device electrode. The electronic control unit is further configured to receive impedance signals from a plurality of passive electrodes. Each of the passive electrodes comprises one of the plurality of measurement electrodes other than one of the pair of active electrodes. Each of the impedance signals is indicative of an impedance at one of the plurality of passive electrodes. The electronic control unit is further configured to establish a virtual reference electrode at a reference position within the body responsive to the impedance signals. The electronic control unit is further configured to generate a position value responsive to the first voltage on the device electrode and the reference position of the reference electrode and to scale the position value using a scaling value computed in response to the impedance signals.

An article of manufacture in accordance with one embodiment of the present teachings includes a computer readable storage medium having a computer program encoded thereon that, when executed by an electronic control unit, determines one or more characteristics of a device electrode disposed on a medical device within a body. The computer program includes code for causing transmission of a current between a pair of active electrodes. The pair of active electrodes is selected from among a plurality of measurements electrodes each coupled to an external surface of the body. The transmission of current between the active electrodes generates a voltage on the device electrode. The computer program further includes code for receiving impedance signals from a plurality of passive electrodes. Each of the passive electrodes comprises one of the plurality of measurement electrodes other than one of the pair of active electrodes. Each of the impedance signals is indicative of an impedance at one of the plurality of passive electrodes. The computer program further includes code for establishing a virtual reference electrode at a reference position within the body responsive to the impedance signals. The computer program further includes code for generating a position value responsive to the first voltage on the device electrode and the reference position of the reference electrode and scaling the position value using a scaling value computed in response to the impedance signals.

A method in accordance with one embodiment of the present teachings for determining one or more characteristics of a device electrode disposed on a medical device within a body includes causing transmission of a current between a pair of active electrodes. The pair of active electrodes is selected from among a plurality of measurements electrodes each coupled to an external surface of the body. The transmission of current between the active electrodes generates a voltage on the device electrode. The method further includes receiving impedance signals from a plurality of passive electrodes. Each of the passive electrodes comprises one of the plurality of measurement electrodes other than one of the pair of active electrodes. Each of the impedance signals is indicative of an impedance at one of the plurality of passive electrodes. The method further includes establishing a virtual reference electrode at a reference position within the body responsive to the impedance signals. The method further includes generating a position value responsive to the first voltage on the device electrode and the reference position of the reference electrode and scaling the position value using a scaling value computed in response to the impedance signals.

A system and method in accordance with the present teachings enable consistent correction of errors in position and impedance measurements due to shift or drift in patient impedance levels. Further, the system and method do not require the use of an additional reference catheter and the resulting increases in procedure time and risks.

The foregoing and other aspects, features, details, utilities, and advantages of the present disclosure will be apparent from reading the following description and claims, and from reviewing the accompanying drawings.

DETAILED DESCRIPTION

Figure 1:
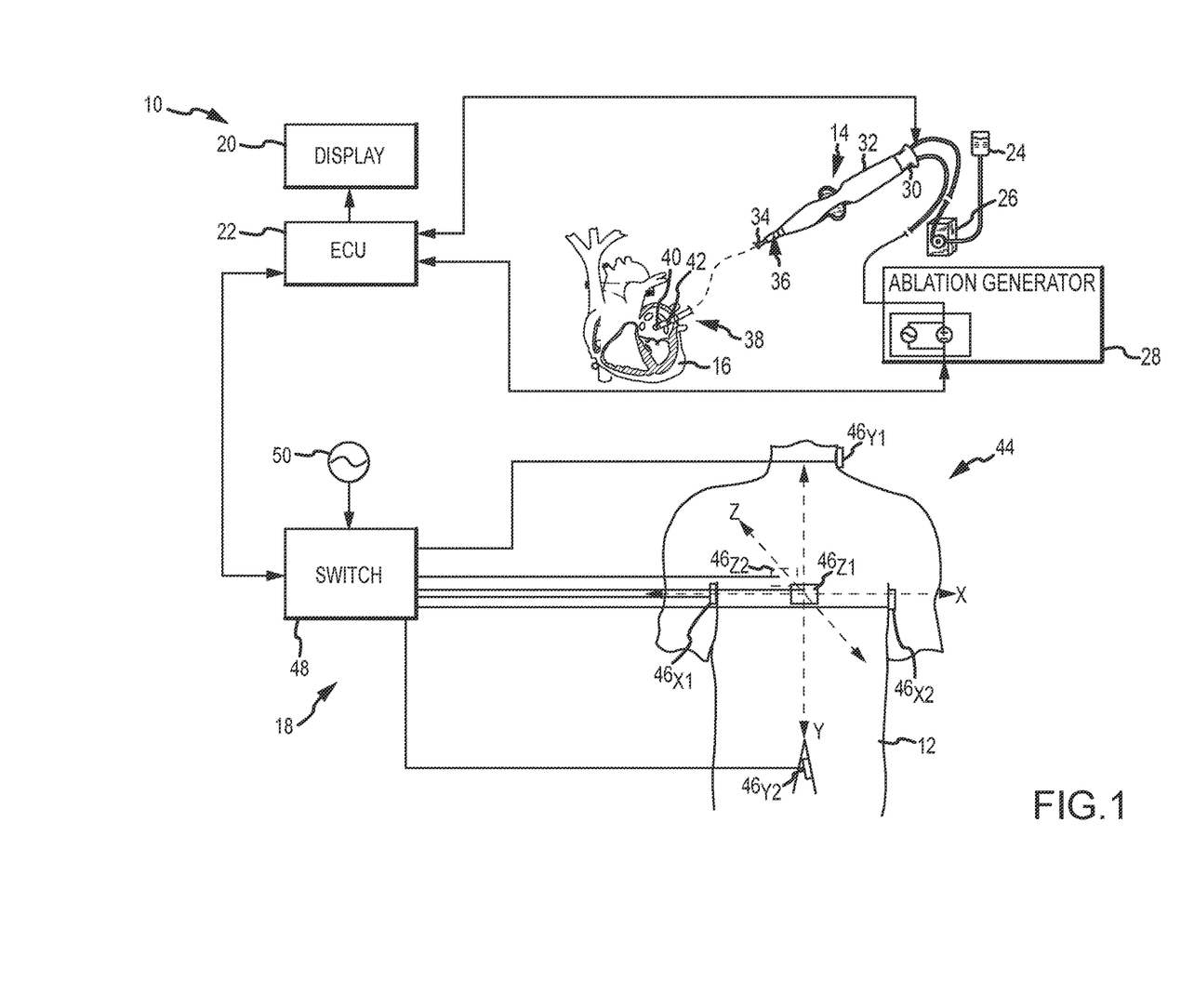
FIG. 1 is diagrammatic view of one embodiment of a system for determining one or more characteristics of a device electrode disposed on a medical device within a body in accordance with the present teachings.

Referring now to the drawings wherein like reference numerals are used to identify identical components in the various views, FIG. 1 illustrates one embodiment of a system 10 for determining one or more characteristics of an electrode disposed on a medical device within a body 12. In the illustrated embodiment, the medical device comprises a catheter 14 and, in particular, an irrigated ablation catheter for use in diagnosis or treatment of cardiac tissue 16 in body 12. It should be understood, however, that a system 10 in accordance with the present teachings may find application in connection with a wide variety of medical devices used within body 12 for diagnosis or treatment. Further, it should be understood that the system 10 may be used with medical devices used in the diagnosis or treatment of portions of body 12 other than the tissue 16. In the embodiment shown in FIG. 1, system 10 includes an electric field based positioning system 18 a display 20, and an electronic control unit (ECU) 22.

Catheter 14 is provided for examination, diagnosis and treatment of internal body tissues such as cardiac tissue 16. In accordance with one embodiment, catheter 14 comprises an ablation catheter and, more particularly, an irrigated radio-frequency (RF) ablation catheter. It should again be understood, however, that catheter 14 is provided for illustration only and that system 10 could be adapted for use with a variety of catheters including, for example, electrophysiology mapping catheters and intracardiac echocardiograph (ICE) catheters, as well as for use with other types of ablation catheters including those providing different types of ablation energy (e.g., cryoablation, ultrasound, etc.). Catheter 14 is connected to a fluid source 24 having a biocompatible fluid such as saline through a pump 26 (which may comprise, for example, a fixed rate roller pump or variable volume syringe pump with a gravity feed supply from fluid source 24 as shown) for irrigation. Catheter 14 is also electrically connected to an ablation generator 28 for delivery of RF energy. Catheter 14 may include a cable connector or interface 30, a handle 32, a shaft 34 having a proximal end 36 and a distal end 38, and one or more device electrodes 40, 42. Catheter 14 may also include other conventional components not illustrated herein such as a temperature sensor, additional electrodes, and corresponding conductors or leads.

Connector 30 provides mechanical, fluid and electrical connection(s) for conduits or cables extending from pump 26 and ablation generator 28. Connector 30 is conventional in the art and is disposed at the proximal end 36 of catheter 14.

Handle 32 provides a location for the physician to hold catheter 14 and may further provides a means for steering or guiding shaft 34 within the body 12. For example, handle 32 may include means to change the length of a guide wire extending through catheter 14 to distal end 38 of shaft 34 to steer distal end 38 and, thus, shaft 34. Handle 32 is also conventional in the art and it will be understood that the construction of handle 32 may vary.

Shaft 34 is an elongated, flexible member configured for movement within body 12. Shaft 34 supports electrodes 40, 42, associated conductors, and, in some embodiments, additional electronics used for signal processing or conditioning. Shaft 34 may also permit transport, delivery, and/or removal of fluids (including irrigation fluids and bodily fluids), medicines, and/or surgical tools or instruments. Shaft 34 may be made from conventional materials such as polyurethane and defines one or more lumens configured to house and/or transport electrical conductors, fluids, or surgical tools. Shaft 34 may be introduced into a blood vessel or other structure within body 12 through a conventional introducer sheath. Shaft 34 may then be steered or guided through body 12 to a desired location such as tissue 16 using guide wires or pull wires or other means known in the art including remote control guidance systems.

Device electrodes 40, 42 may be provided for a variety of diagnostic and therapeutic purposes including, for example, electrophysiological studies, catheter identification and location, pacing, and cardiac mapping and ablation. Electrodes 40, 42 may also be provided for use in determining the position of catheter 14 within body 12. In the illustrated embodiment, catheter 14 includes an ablation tip electrode 40 at distal end 38 of shaft 34 and one more ring electrodes 42 located proximal to the tip electrode. It should be understood, however, that the number, orientation, and purpose of electrodes 40, 42 may vary. As electrodes 40, 42 move within body 14, and within the electric field generated by system 18, the voltage readings from electrodes 40, 42 change thereby indicating the location of electrodes 40, 42 within the electric field and with a coordinate system 44 established by system 18. Electrodes 40, 42 communicate signals to ECU 22 through a conventional interface (not shown).

System 18 is provided to determine the position and orientation of catheter 14 and similar devices within body 12. System 18 may comprise a portion or all of the system made available under the trademark "ENSITE NAVX" by St. Jude Medical, Inc. and described, for example, in U.S. Pat. No. 7,263,397 titled "Method and Apparatus for Catheter Navigation and Location Mapping in the Heart," the entire disclosure of which is incorporated herein by reference. The system 18 is based on the principle that when low amplitude electrical signals are passed through the thorax, body 12 acts as a voltage divider (or potentiometer or rheostat) such that the electrical potential or field strength measured at an electrode such as one of device electrodes 40, 42 on catheter 14 may be used to determine the position of the electrode, and therefore catheter 14, relative to a pair of external measurement electrodes using Ohm's law and the relative location of a reference electrode (e.g. in the coronary sinus). In one configuration, the system includes three pairs of measurement electrodes 46 that are placed on opposed surfaces of body 12 (e.g., chest and back, left and right sides of the thorax, and neck and leg) and form generally orthogonal x, y, and z axes. The system 18 also typically includes a reference electrode/patch that is typically placed near the belly of the patient and provides an impedance reference value and may act as the origin of the coordinate system 44 for the navigation system. In accordance with one aspect of the present teachings discussed in greater detail below, however, a virtual reference electrode within body 12 may replace the external reference electrode/patch as the origin of coordinate system 44 and, further, the impedance reference may be relocated and even be disposed within body 12 for improved compensation of drift and shifts. Sinusoidal currents are driven through each pair of measurement electrodes 46 and voltage measurements for one or more device electrodes 40, 42 associated with catheter 14 are obtained. The measured voltages are a function of the distance of the device electrodes 40, 42 from the measurement electrodes 46. The measured voltages may be compared to a position reference such as the virtual reference electrode described in greater detail below and a position of the electrodes 40, 42 within the coordinate system 44 of the navigation system may be determined. In accordance with this exemplary system, system 18 may include measurement electrodes 46 (namely $46_{X1}$, $46_{X2}$, $46_{Y1}$, $46_{Y2}$, $46_{Z1}$, $46_{Z2}$) a switch 48, and a signal generator 50.

Measurement electrodes 46 are provided to generate electrical signals used in determining the position of catheter 14 within three-dimensional coordinate system 44 of system 18. Electrodes 46 may also be used to generate EP data regarding tissue 16. Electrodes 46 may comprise patch electrodes having a flexible substrate and which are affixed to the surface of body 12 using adhesives. Electrodes 46 are placed orthogonally on the surface of body 12 and are used to create axes specific electric fields within body 12. Electrodes $46_{X1}$, $46_{X2}$ may be placed along a first (x) axis. Similarly, electrodes $46_{Y1}$, $46_{Y2}$ may be placed along a second (y) axis, and electrodes $46_{Z1}$, $46_{Z2}$ may be placed along a third (z) axis. Each of the electrodes 46 may be coupled to multiplex switch 48. ECU 22 is configured through appropriate software and/or hardware to provide control signals to switch 48 and thereby sequentially couple pairs of electrodes 46 to signal generator 50 in order to form active or driven electrode pairs. Excitation of each active pair of electrodes 46 generates an electromagnetic field within body 14 and within an area of interest such as the heart. Voltage levels at passive or non-driven electrodes 46 may be filtered and converted and provided to ECU 22 for use as reference values and, in particular, to establish a virtual reference electrode as discussed in greater detail below.

Display 20 is provided to convey information to a physician to assist in diagnosis and treatment. Display 20 may comprise one or more conventional computer monitors or other display devices. Display 20 may present a graphical user interface (GUI) to the physician. The GUI may include a variety of information including, for example, an image of the geometry of tissue 16, electrophysiology data associated with the tissue 16, graphs illustrating voltage levels over time for various electrodes 40, 42, and images of catheter 14 and other medical devices and related information indicative of the position of catheter 14 and other devices relative to the tissue 16.

ECU 22 provides a means for controlling the operation of various components of system 10 including catheter 14 and ablation generator 28 and switch 48 of system 18. ECU 22 may also provide a means for determining the geometry of tissue 16, electrophysiology characteristics of tissue 16 and the position and orientation of catheter 14 relative to tissue 16 and body 12. ECU 22 also provides a means for generating display signals used to control display 20. ECU 22 may comprise one or more programmable microprocessors or microcontrollers or may comprise one or more application specific integrated circuits (ASICs). ECU 22 may include a central processing unit (CPU) and an input/output (I/O) interface through which ECU 22 may receive a plurality of input signals including signals generated by ablation generator 28, device electrodes 40, 42 on catheter 14, and measurement electrodes 46 of system 18. The CPU and I/O interface of the ECU 22 is also configured to generate a plurality of output signals including those used to control and/or provide data to catheter 14, display 20, ablation generator 28, switch 48 of system 18, and generator 50 of system 20.

In accordance with the present teachings, ECU 22 may be configured with programming instructions from a computer program (i.e., software) to implement a method for determining one or more characteristics of a device electrode 40, 42 on a medical device such as catheter 14 with body 12. The program may be stored in a computer storage medium such as a memory (not shown) that is internal to ECU 22 or external to ECU 22, and may be pre-installed in the memory or obtained from a computer storage medium external to ECU 22 including from various types of portable media (e.g., compact discs, flash drives, etc.) or file servers or other computing devices accessible through a telecommunications network.

Figure 2:
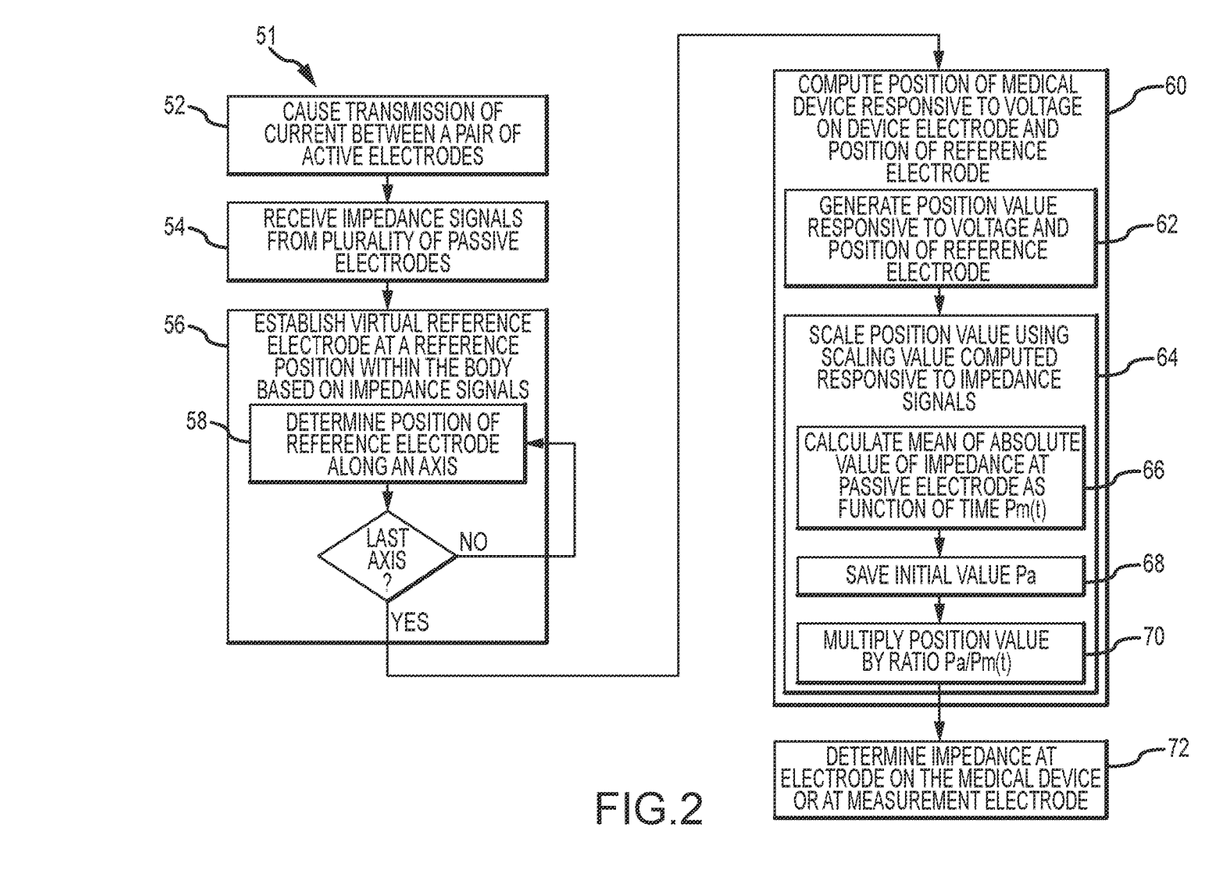
FIG. 2 is a flow-chart diagram illustrating one embodiment of a method for determining one or more characteristics of a device electrode disposed on a medical device within a body in accordance with the present teachings.

FIG. 2 is a flow-chart diagram illustrating one embodiment of a method for determining one or more characteristics of a device electrode disposed on a medical device. As shown in FIG. 2, the method 51 may begin generally with the process 52 of causing transmission of current between a pair of measurement electrodes 46. ECU 22 may generate control signals and transmit these signals to switch 48 to couple selected pairs of electrodes 46 to signal generator 50. Hereinafter, the measurement electrodes 46 across which current is transmitted at any given point in time may be referred to as active or driven electrodes. The other measurement electrodes 46 may be referred to as passive or non-driven electrodes. As described hereinabove, transmission of current across a given pair of measurement electrodes 46 will generate a voltage on device electrodes 40, 42. Electrodes 40, 42 will generate signals indicative of the voltage which may be transmitted to ECU 22 through conductors in device 12, through interface 30 and finally through conventional conductors extending between interface 30 and ECU 22.

The method may continue with the process 54 of receiving impedance signals from a plurality of passive electrodes 46. The impedance signals are indicative of a measured impedance at the passive electrodes 46 resulting from the transmission of current across the active electrodes 46. For example, if current is driven across active electrodes 46$_{X1}$, 46$_{X2}$, impedance may be measured at passive electrodes 46$_{Y1}$, 46$_{Y2}$, 46$_{Z1}$, 46$_{Z2}$. Impedance signals may be transmitted from passive electrodes 46 through conventional conductors to ECU 22.

The method may continue with the process 56 of establishing a virtual reference electrode at a reference position within body 14 responsive to the impedance signals received from the passive electrodes 46. The virtual reference electrode is intended to act as a position reference and, in some embodiments, may replace the external reference patch electrode that is typically located near the belly of the patient in the system made available under the trademark "ENSITE NAVX" by St. Jude Medical, Inc. In accordance with one aspect of the present teachings, the virtual reference electrode is located within body 14 and nearer to electrodes 40, 42 relative to the conventional external reference patch electrode. As a result, the reference electrode is more centrally located relative to axes on which currents are transmitted and body resistance between the electrodes 40, 42 and the reference electrode—which varies along each axis—is reduced or eliminated thereby reducing measurement errors.

Process 56 may include the subprocess 58 of determining a position for the virtual reference electrode along an axis extending through body 14. This subprocess may be repeated for additional axes. Referring to FIG. 1, for example, the position for the virtual reference electrode along the x-axis within coordinate system 44 may be determined, along with the position along the y-axis perpendicular to the x-axis and the z-axis which is perpendicular to both the x-axis and y-axis in order to arrive at a three dimensional coordinate for the virtual reference electrode. The position of the virtual reference electrode along any individual axis may be determined using impedance signals from passive electrodes 46. Like electrodes 40, 42, the position of each individual measurement electrode 46 within coordinate system 44 may be located using system 18. Due, however, to large impedances at the interface between the electrodes 46 and the skin surface of body 14 and the generation of large electrical potentials resulting from the application of constant current through the interface, the measured position of electrodes 46 will be located relatively far from the geometric center of the electrodes 46 within body 14. Notably though, the measured position for each measurement electrode 46 will be relatively far from the geometric center on certain axes, but relatively close on other axes. For electrodes 46$_{X1}$, 46$_{X2}$, the measured position is relatively far from the center along the x-axis in FIG. 1, but relatively close to the center along the y and z axes. Similarly, for electrodes 46$_{Y1}$, 46$_{Y2}$, the measured position is relatively far from the center along the y-axis in FIG. 1, but relatively close to the center along the x and z axes while for electrodes 46$_{Z1}$, 46$_{Z2}$, the measured position is relatively far from the center along the z-axis, but relatively close to the center along the x and y axes. The position coordinates for each electrode 46 that are relatively close to the geometric center coincide with those positional coordinates measured when the electrode 46 is acting as a passive electrode. As a result, measurements made on various pairs of electrodes 46 when electrodes 46 are acting as passive electrodes can be used to establish a center point along each axis and, therefore, a virtual reference electrode at a geometric center within body 14. In general, to establish a center point along any individual axis, impedance measurements are taken at two or more measurement electrodes 46 (excluding those measurement electrodes 46 that are used to transmit current along the subject axis) when such measurement electrodes 46 are functioning as passive electrodes (although, at times, measurements made when functioning as active electrodes may be used as noted below) and are averaged as indicated in the following expression:

$$(IMP[46_1]+IMP[46_2]+\ldots IMP[46_N])/N \quad (1)$$

where $IMP[46_1] \ldots IMP[46_1]$ represent impedances measured as N measurement electrodes. For example, in one particular embodiment, measurements made on electrodes 46$_{X1}$, 46$_{X2}$ when electrodes 46$_{X1}$, 46$_{X2}$ are passive electrodes can be used to establish a virtual position along the z-axis while measurements made on electrodes 46$_{Z1}$, 46$_{Z2}$ when electrodes 46$_{Z1}$, 46$_{Z2}$ are passive electrodes can be used to establish a virtual position along the x-axis and measurements on electrodes 46$_{Z1}$, 46$_{X1}$, 46$_{X2}$ when electrodes 46$_{Z1}$, 46$_{X1}$, 46$_{X2}$ are passive electrodes can be used to establish a virtual position along the y-axis. In particular, the following equations may be used to determine the position of the virtual reference electrode along each axis:

$$X_{REF}=(IMP[46_{Z2}][46_{X1}:46_{Z1}]+IMP[46_{Z2}][46_{Z1}: \\ 46_{X2}]-IMP[46_{Z1}][46_{Z2}:46_{X1}]-IMP[46_{Z1}][46_{X2}: \\ 46_{Z2}])/2/Xscale \quad (2)$$

$$Y_{REF}=(IMP[46_{X1}][46_{Y1}:46_{Z2}]-IMP[46_{X1}][46_{Y2}: \\ 46_{Z2}]+IMP[46_{X2}][46_{Y1}:46_{Z2}]-IMP[46_{X2}][46_{Y2}: \\ 46_{Z2}]+IMP[46_{Z1}][46_{Y1}:46_{Z2}]-IMP[46_{Z1}][46_{Y2}: \\ 46_{Z2}])/3/Yscale \quad (3)$$

$$Z_{REF}=(IMP[46_{X2}][46_{X1}:46_{Z1}]+IMP[46_{X2}][46_{Z2}: \\ 46_{X1}]-IMP[46_{X1}][46_{Z1}:46_{X2}]-IMP[46_{X1}][46_{X2}: \\ 46_{Z2}])/2/Zscale \quad (4)$$

Where IMP[i][U] represents the impedance measured on an electrode i during transmission of current across an electrode pair j from the first listed electrode to the second listed electrode and Xscale, Yscale, and Zscale are scaling factors used to convert the unit of measurement to a measure of distance (e.g., millimeters). Thus, the subprocess 58 of determining the position along a given axis may include subprocesses of summing impedances at a subset of passive electrodes 46 to obtain a cumulative impedance value, dividing the cumulative impedance value by the number of passive electrodes in the subset and scaling the resulting value. It should be understood that the above equations are exemplary and that a variety of different equations could be formed for any given axis using impedance measurements at passive electrodes 46 that do not lie along the given axis resulting from the excitation of various pairs of active electrodes 46. For example, the position of the virtual reference electrode along the y-axis could alternatively be computed as follows:

$$Y_{REF} = (IMP[46_{X1}][46_{Y1}:46_{Z2}] - IMP[46_{X1}][46_{Y2}: \\ 46_{Z2}] + IMP[46_{Y1}][46_{Z1}:46_{Z2}] - IMP[46_{Z1}][46_{Y2}: \\ 46_{Z2}] + IMP[46_{Z2}][46_{Y1}:46_{Z2}] - IMP[46_{Z2}][46_{Y2}: \\ 46_{Z2}])/3/Yscale \quad (5)$$

Although equation (5) includes impedances measured at active electrodes (i.e. IMP[$46_{Z2}$][$46_{Y1}:46_{Z2}$] and IMP[$46_{Z2}$] [$46_{Y2}:46_{Z2}$]), the impedances are effectively subtracted.

The method may continue with the process 60 of computing a position of the medical device 14 responsive to the voltage on electrode 40 or 42 and the reference position of the virtual reference electrode determined in process 56. Process 60 may include the subprocess 62 of generating a position value responsive to the voltage on the device electrode 40 or 42 and the reference position of the reference electrode. In general, the position along a given axis may be determined by subtracting the position of the virtual reference electrode along that axis from the position of the device electrode 40, 42 along that axis as indicated in the following equation relating to the x-axis:

$$X\_corr = X - (IMP[46_1] + IMP[46_2] + \ldots IMP[46_N])/N \quad (6)$$

where X represents the uncorrected position along the x-axis of the device electrode 40, 42 as determined by the voltage on electrode 40 or 42 and IMP[$46_1$] . . . IMP[$46_N$] represent impedance measurements on N measurement electrodes 46 as described hereinabove in equation (1). The expression (IMP[$46_1$]+IMP[$46_2$]+ . . . IMP[$46_N$])/N may essentially be replaced, in one embodiment, by $X_{REF}$ from equation (2) above. Thus, for example, a position value along three axes may be calculated using the following equations:

$$X\_corr = X - X_{REF} + X_{REF}[0] \quad (7)$$

$$Y\_corr = Y - Y_{REF} + Y_{REF}[0] \quad (8)$$

$$Z\_corr = Z - Z_{REF} + Z_{REF}[0] \quad (9)$$

where X, Y, and Z represent the uncorrected positions along the x-axis, y-axis, and z-axis of the device electrode 40 or 42 as determined by the voltage on electrode 40 or 42, $X_{REF}$, $Y_{REF}$, and $Z_{REF}$ represent the positions along the x-axis, y-axis and z-axis of the virtual reference electrode as determined from equations (2)-(4) above and $X_{REF}[0]$, $Y_{REF}[0]$, and $Z_{REF}[0]$ represent initial values that may be optionally added in order to preserve the range of the navigation domain. The system compensates for drift due to changes in body impedance because the location of the virtual reference electrode, unlike traditional position references, is impacted by drift in the same manner as the measured position of device electrodes 40, 42. In some embodiments, a finer degree of compensation can be achieved by also applying bio-impedance scaling, as indicated generally at block 60. Accordingly, process 60 may further include the subprocess 64 of scaling the position value using a scaling value computed in response to the impedance signals. ECU 22 may compute a scaling value BioZscale using, for example, the methodology described in U.S. Pat. No. 7,885,707, the entire disclosure of which is incorporated herein by reference. Accordingly, subprocess 64 may include the subprocess 66 of calculating a mean of an absolute value of an impedance at one of the passive electrodes 46 continuously as a function of time to obtain a value Pm(t). Subprocess 64 may further include the subprocess 68 of saving an initial calculated mean of the absolute value of the impedance as a value Pa. Subprocess 64 may further include the subprocess 70 of multiplying the position value obtained in subprocess 62 by the ratio Pa/Pm(t), or BioZscale. In particular, equations (7)-(9)) above may be modified as follows:

$$X\_corr = (X - X_{REF}) * \text{BioZscale} + X_{REF}[0] \quad (10)$$

$$Y\_corr = (Y - Y_{REF}) * \text{BioZscale} + Y_{REF}[0] \quad (11)$$

$$Z\_corr = (Z - Z_{REF}) * \text{BioZscale} + Z_{REF}[0] \quad (12)$$

Equations (10)-(12) will account for any differences in scaling between the determined positions of device electrodes 40, 42 and the virtual reference electrode. Subprocesses 64, 66, 68 may be performed for each pair of active electrodes to generate separate scaling factors for each pair of active electrodes with the understanding that impedance changes may not be homogenous within body 12. Alternatively, subprocesses 64, 66, 68 may result in a common scaling factor under the assumption that any biologic impedances changes are essentially homogenous within body 12.

In accordance with one aspect of the above-described system 10 and method, the impedance reference may be located anywhere within the navigational field without affecting the position measurements. Because the virtual reference electrode now functions as a positional reference, the position and impedance reference functions that are sometimes combined in a single device (such as external reference (belly) electrode/patch referenced hereinabove) are no longer co-dependent. Equation (6), for example, may be rewritten as follows such that it is not dependent on the potential of the impedance reference because the potential of the impedance reference is subtracted from all quantities of interest:

$$X\_corr = ((X - IMP[46_1]) + (X - IMP[46_2]) + \ldots (X - IMP[46_N]))/N \quad (13)$$

Since every measurement in every term in the Equation (13) is taken with respect to the impedance reference, the impedance reference contribution is exactly cancelled in every term. The impedance reference may therefore be moved without impacting position measurements.

A method in accordance with the present teachings may further include the process 72 of determining an impedance at an electrode on device 14 such as electrode 40 or 42 or at another electrode within system 18 such as any of measurement electrodes 46. Process 72 may include the subprocess of computing the impedance responsive to an impedance indicative signal generated by electrode 40, 42 or 46 and another impedance indicative signal generated by an impedance reference electrode. As noted above, in accordance with one aspect of the invention, the impedance reference may be moved anywhere within the navigational domain without impacting location measurements. Accordingly, the impedance reference may be disposed on another medical device within the body including, for example, another catheter such as a coronary sinus catheter. ECU 22 may receive signals indicative of the impedance at device electrode 40, 42 or measurement electrode 46 and from an electrode on the coronary sinus catheter and determine an impedance at the device electrode 40, 42 or measurement electrode 46 in response to these signals.

A system 10 and method in accordance with the present teachings enable consistent correction or errors in position and impedance measurements due to shift or drift in patient impedance levels. Further, the system 10 and method do not require the use of an additional reference catheter and the resulting increases in procedure time and risks.

The disclosed system and method were tested by applying the disclosed methodology to recorded position information for an implanted coronary sinus catheter electrode. Drift in position values for the catheter electrode using the disclosed methods was compared to drift in position values without any attempt to compensate for drift, to drift in position values where bio impedance scaling was used in an attempt to compensate for drift, and to drift where both bio impedance scaling and a virtual reference electrode was used. Drift was estimated by the slope of the linear fit applied to data along the z-axis yielding the following results:

TABLE 1

| Method of Compensation | Slope (mm/hour) |
| --- | --- |
| No compensation | 17.3 |
| Compensation with bio-impedance scaling | 5.5 |
| Compensation with use of virtual reference electrode and bio-impedance scaling (see, e.g., Equations (10)-(12)) | 4.0 |

Figure 3:
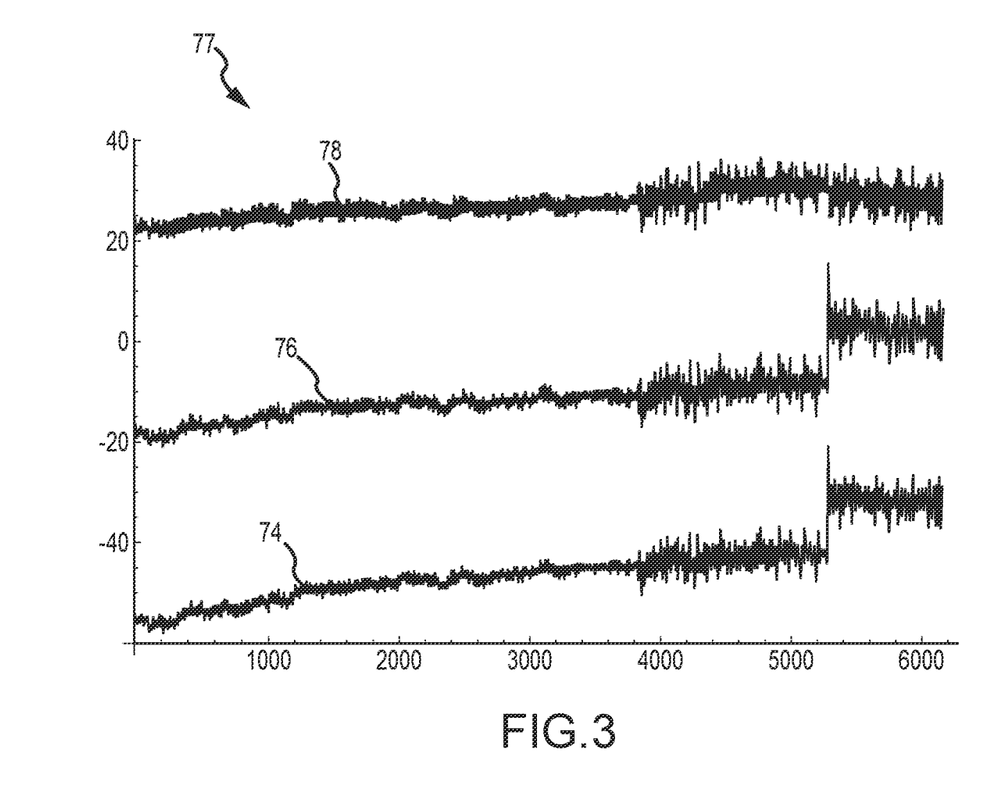
FIG. 3 is a graph illustrating position over time for a device electrode disposed on a medical device within a body in the absence of any shift compensation, with shift compensation based on bio-impedance scaling, and with shift compensation in accordance with the present teachings.

FIG. 3 is a graph 77 illustrating several exemplary traces for a device electrode disposed on a medical device within a body in the absence of any shift compensation, with shift compensation based on bio-impedance scaling, and with shift compensation in accordance with the present teachings. The traces in FIG. 3 represent, for example, how a shift in impedance on a measurement electrode 46 can result in a shift of position values for a device electrode along the x-axis. Trace 78 represents the position of the electrode without compensation for drift or shift. Trace 80 represents the position of the electrode with compensation through bio-impedance scaling and continues to exhibit a relatively large shift in position. Trace 82 represents the position of the electrode with compensation based on the use of a virtual reference electrode and bio-impedance scaling as described hereinabove. As shown in the example in Table 1 and in the example traces 78, 80, 82 depicted in FIG. 3, the use of the inventive system and method achieved improved compensation for impedance shift.

Although several embodiments of a system in accordance with present teachings have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the disclosed embodiments, and do not create limitations, particularly as to the position, orientation, or use of the disclosed embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the present teachings as defined in the appended claims.

What is claimed is:

1. A medical device system comprising:
a first medical device having a device electrode;
a plurality of measurement electrodes configured for coupling to an external surface of a body, the plurality of measurement electrodes including an impedance reference electrode; and
a controller configured to:
establish a virtual reference electrode using the plurality of measurement electrodes;
generate a position value for the device electrode relative to the virtual reference electrode and responsive to an impedance indicative signal generated by the impedance reference electrode; and
scale the position value using a scaling value.

2. The medical device system of claim 1 wherein the virtual reference electrode is at a geometric center of the measurement electrodes.

3. The medical device system of claim 1 wherein the scaling value comprises a BioZscale scaling value.

4. The medical device system of claim 1 wherein the position value is generated in response to a first voltage on the device electrode and a reference position of the virtual reference electrode.

5. The medical device system of claim 4 wherein the controller is further configured to:
cause transmission of a current between a first pair of active electrodes selected from the measurement electrodes to thereby generate the first voltage on the device electrode; and
receive impedance signals from a plurality of passive electrodes selected from non-active measurement electrodes, each of the impedance signals indicative of an impedance at one of the plurality of passive electrodes.

6. The medical device system of claim 5 wherein the virtual reference electrode is established at the reference position in response to the impedance signals.

7. The medical device system of claim 5 wherein the scaling value is computed in response to the impedance signals.

8. The medical device system of claim 5 wherein the controller is further configured, in scaling the position value, to: calculate a mean of an absolute value of an impedance at one of the plurality of passive electrodes continuously as a function of time Pm(t); save an initial calculated mean of the absolute value of the impedance as Pa; and, multiply the position value by the ratio Pa/Pm(t).

9. The medical device system of claim 5 wherein the controller is further configured, in establishing the virtual reference electrode at the reference position, to: determine a position for the virtual reference electrode along a first axis; determine a position for the virtual reference electrode along a second axis perpendicular to the first-axis; and, determine a position for the virtual reference electrode along a third axis perpendicular to the first axis and the second axis.

10. The medical device system of claim 9 wherein the controller is further configured, in determining a position for the virtual reference electrode along the first axis to: sum impedances at a subset of passive electrodes of the plurality of passive electrodes to obtain a cumulative impedance value; and, divide the cumulative impedance value by the number of the passive electrodes in the subset of passive electrodes.

11. The medical device system of claim 1 wherein the impedance reference electrode is disposed on a second medical device.

12. The medical device system of claim 1 wherein the impedance reference electrode comprises a measurement electrode.

13. The medical device system of claim 5, wherein said controller is further configured to determine an impedance at said device electrode.

14. The medical device system of claim 13, wherein said controller is further configured, in determining said impedance, to compute said impedance responsive to a first impedance indicative signal generated by said device electrode and a second impedance indicative signal generated by an impedance reference electrode.

15. The medical device system of claim 13, wherein said controller is further configured to determine an impedance at a first passive electrode of said plurality of passive electrodes responsive to said impedance signal generated by said first passive electrode and an impedance indicative signal generated by an impedance reference electrode.

* * * * *